US011179322B2

(12) United States Patent
Gotlib et al.

(10) Patent No.: US 11,179,322 B2
(45) Date of Patent: Nov. 23, 2021

(54) METHODS AND COMPOSITIONS FOR TREATING TUMORS WITH TTFIELDS AND SORAFENIB

(71) Applicant: Novocure GmbH, Root (CH)

(72) Inventors: Karnit Gotlib, Tirat Carmet (IL); Einav Zeevi, Zichron Yaakov (IL); Rosa S. Schnaiderman, Haifa (IL); Tali Voloshin-Sela, Kibbutz Gvat (IL); Moshe Giladi, Moshav Herut (IL); Adrian Kinzel, Bochum (DE); Eilon Kirson, Ramat Hasharon (IL); Uri Weinberg, Binyamina (IL); Yoram Palti, Haifa (IL); Shiri Davidi, D.N. Galil Maharavi (IL)

(73) Assignee: Novocure GmbH, Root (CH)

( * ) Notice: Subject to any disclaimer, the term of this patent is extended or adjusted under 35 U.S.C. 154(b) by 0 days.

(21) Appl. No.: 16/506,008

(22) Filed: Jul. 9, 2019

(65) Prior Publication Data
US 2020/0016067 A1 Jan. 16, 2020

Related U.S. Application Data

(60) Provisional application No. 62/695,918, filed on Jul. 10, 2018.

(51) Int. Cl.
*A61N 1/20* (2006.01)
*A61K 31/4418* (2006.01)
(Continued)

(52) U.S. Cl.
CPC ........ *A61K 9/0009* (2013.01); *A61K 31/4418* (2013.01); *A61N 1/205* (2013.01); *A61P 35/00* (2018.01)

(58) Field of Classification Search
CPC ...... A61K 9/0009; A61K 9/08; A61K 9/0019; A61K 47/10; A61K 47/44; A61K 31/4418; A61N 1/32; A61N 1/205; A61P 35/00
(Continued)

(56) References Cited

U.S. PATENT DOCUMENTS 6,868,289 B2   3/2005  Palti
7,016,725 B2   3/2006  Palti
(Continued)

FOREIGN PATENT DOCUMENTS

WO   WO-2016015015 A1 * 1/2016 ........... A61K 31/337

OTHER PUBLICATIONS

Gennaro Gadaleta-Caldarola et al., Sorafenib and locoregional deep electro-hyperthermia in advanced hepatocellular carcinoma: A phase II study, May 23, 2014, Spandidos Publications UK Ltd, pp. 1783-1787 (Year: 2014).*
(Continued)

*Primary Examiner* — Carl H Layno
*Assistant Examiner* — Anh-Khoa N Dinh
(74) *Attorney, Agent, or Firm* — Potomac Law Group, PLLC

(57) ABSTRACT

Viability of cancer cells (e.g., hepatocellular carcinoma cells) can be reduced by administering sorafenib to the cancer cells and applying an alternating electric field with a frequency between 100 and 400 kHz to the cancer cells. Viability of cancer cells (e.g., hepatocellular carcinoma cells) disposed in a body of a living subject can be reduced by administering sorafenib to the subject and applying an alternating electric field with a frequency between 100 and 400 kHz to the cancer cells. Notably, experiments show that the combination of sorafenib and the alternating electric field produces synergistic results both in vitro and in vivo.

26 Claims, 8 Drawing Sheets

(51) Int. Cl.
*A61K 9/00* (2006.01)
*A61P 35/00* (2006.01)

(58) Field of Classification Search
USPC .................................................. 600/10, 14
See application file for complete search history.

(56) References Cited

U.S. PATENT DOCUMENTS

| | | | |
|---|---|---|---|
| 7,089,054 B2 | 8/2006 | Palti | |
| 7,136,699 B2 | 11/2006 | Palti | |
| 7,146,210 B2 | 12/2006 | Palti | |
| 7,235,576 B1 | 6/2007 | Riedl et al. | |
| 7,333,852 B2 | 2/2008 | Palti | |
| 7,351,834 B1 | 4/2008 | Riedl et al. | |
| 7,467,011 B2 | 12/2008 | Palti | |
| 7,519,420 B2 | 4/2009 | Palti | |
| 7,565,205 B2 | 7/2009 | Palti | |
| 7,565,206 B2 | 7/2009 | Palti | |
| 7,599,745 B2 | 10/2009 | Palti | |
| 7,599,746 B2 | 10/2009 | Palti | |
| 7,706,890 B2 | 4/2010 | Palti | |
| 7,715,921 B2 | 5/2010 | Palti | |
| 7,805,201 B2 | 9/2010 | Palti | |
| 7,890,183 B2 | 2/2011 | Palti et al. | |
| 7,897,623 B2 | 3/2011 | Riedl et al. | |
| 7,912,540 B2 | 3/2011 | Palti | |
| 7,917,227 B2 | 3/2011 | Palti | |
| 8,019,414 B2 | 9/2011 | Palti | |
| 8,027,738 B2 | 9/2011 | Palti | |
| 8,124,630 B2 | 2/2012 | Riedl et al. | |
| 8,170,684 B2 | 5/2012 | Palti | |
| 8,175,698 B2 | 5/2012 | Palti et al. | |
| 8,229,555 B2 | 7/2012 | Palti | |
| RE43,618 E | 8/2012 | Palti | |
| 8,244,345 B2 | 8/2012 | Palti | |
| 8,406,870 B2 | 3/2013 | Palti | |
| 8,447,395 B2 | 5/2013 | Palti et al. | |
| 8,447,396 B2 | 5/2013 | Palti et al. | |
| 8,465,533 B2 | 6/2013 | Palti | |
| 8,618,141 B2 | 12/2013 | Dumas et al. | |
| 8,706,261 B2 | 4/2014 | Palti | |
| 8,715,203 B2 | 5/2014 | Palti | |
| 8,718,756 B2 | 5/2014 | Palti | |
| 8,764,675 B2 | 7/2014 | Palti | |
| 8,841,330 B2 | 9/2014 | Riedl et al. | |
| 8,877,933 B2 | 11/2014 | Grunenberg et al. | |
| 9,023,090 B2 | 5/2015 | Palti | |
| 9,023,091 B2 | 5/2015 | Palti | |
| 9,039,674 B2 | 5/2015 | Palti et al. | |
| 9,056,203 B2 | 6/2015 | Palti et al. | |
| 9,440,068 B2 | 9/2016 | Palti et al. | |
| 9,655,669 B2 | 5/2017 | Palti et al. | |
| 9,737,488 B2 | 8/2017 | Schückler et al. | |
| 9,750,934 B2 | 9/2017 | Palti et al. | |
| 9,910,453 B2 | 3/2018 | Wasserman et al. | |
| 10,188,851 B2 | 1/2019 | Wenger et al. | |
| 10,441,776 B2 | 10/2019 | Kirson et al. | |
| 2007/0239213 A1* | 10/2007 | Palti ................. | A61N 1/40 607/3 |
| 2014/0302030 A1* | 10/2014 | Kim ................. | A61K 39/39558 424/135.1 |
| 2017/0120041 A1 | 5/2017 | Wenger et al. | |
| 2017/0215939 A1 | 8/2017 | Palti et al. | |
| 2017/0281934 A1 | 10/2017 | Giladi et al. | |
| 2018/0001075 A1 | 1/2018 | Kirson et al. | |
| 2018/0008708 A1 | 1/2018 | Giladi et al. | |
| 2018/0050200 A1 | 2/2018 | Wasserman et al. | |
| 2018/0160933 A1 | 6/2018 | Urman et al. | |
| 2018/0202991 A1 | 7/2018 | Giladi et al. | |
| 2019/0117956 A1 | 4/2019 | Wenger et al. | |
| 2019/0298982 A1 | 10/2019 | Story et al. | |
| 2019/0307781 A1 | 10/2019 | Krex et al. | |
| 2019/0308016 A1 | 10/2019 | Wenger et al. | |

OTHER PUBLICATIONS

Giladi et al., "Mitotic Spindle Disruption by Alternating Electric Fields Leads to Improper Chromosome Segregation and Mitotic Catastrophe in Cancer Cells," Scientific Reports, vol. 5, p. 18046, Dec. 2015.

Laufer et al., "Electrical impedance characterization of normal and cancerous human hepatic tissue," Physiological Measurement, vol. 31, No. 7, pp. 995-1009, Jul. 2010.

Bruggmoser et al., "Quality Assurance for Clinical Studies in Regional Deep Hyperthermia," Strahlentherapie und Onkologie, 2011, vol. 187(10), p. 605-610, Springer.

Szasz et al., "Oncothermia protocol," Oncothermia Journal, 2013, vol. 8, pp. 13-45, Springer Verlag, Berlin, Germany.

* cited by examiner

METHODS AND COMPOSITIONS FOR TREATING TUMORS WITH TTFIELDS AND SORAFENIB

CROSS-REFERENCE TO RELATED APPLICATIONS

This application claims the benefit of U.S. Provisional Patent Application No. 62/695,918, filed Jul. 10, 2018, which is incorporated herein by reference in its entirety.

BACKGROUND

Tumor Treating Fields (TTFields) are an effective antineoplastic treatment modality delivered via non-invasive application of low intensity, intermediate frequency, alternating electric fields. TTFields exert directional forces on polar microtubules and interfere with the normal assembly of the mitotic spindle. Such interference with microtubule dynamics results in abnormal spindle formation and subsequent mitotic arrest or delay. Cells can die while in mitotic arrest or progress to cell division leading to the formation of either normal or abnormal aneuploid progeny. The formation of tetraploid cells can occur either due to mitotic exit through slippage or can occur during improper cell division. Abnormal daughter cells can die in the subsequent interphase, can undergo a permanent arrest, or can proliferate through additional mitosis where they will be subjected to further TTFields assault (FIG. 1). Giladi M et al. *Sci Rep.* 2015; 5:18046.

TTFields therapy is delivered using a wearable and portable device (Optune®). The delivery system includes an electric field generator, four adhesive patches (non-invasive, insulated transducer arrays), rechargeable batteries and a carrying case. The transducer arrays are applied to the skin and are connected to the device and battery. The therapy is designed to be worn for as many hours as possible throughout the day and night.

In the preclinical setting, TTFields can be applied in vitro using, for example, the Inovitro™ TTFields lab bench system. Inovitro™ includes a TTFields generator and base plate containing 8 ceramic dishes per plate. Cells are plated on a 22 mm round cover slip placed inside each dish. TTFields are applied using two perpendicular pairs of transducer arrays insulated by a high dielectric constant ceramic in each dish. The orientation of the TTFields in each dish is switched 90° every 1 second, thus covering the majority of the orientation axes of cell divisions.

SUMMARY

The inventors have determined that treating hepatocellular carcinoma (HCC) with the combination of sorafenib and TTFields provides a synergistic result.

One aspect of the invention is directed to a first method of reducing viability of cancer cells. The first method comprises administering sorafenib to the cancer cells; and applying an alternating electric field to the cancer cells, the alternating electric field having a frequency between 100 and 400 kHz.

In some instances of the first method, the frequency of the alternating electric field is between 120 and 180 kHz. In some instances of the first method, at least a portion of the applying step is performed simultaneously with at least a portion of the administering step. In some instances of the first method, the cancer cells comprise hepatocellular carcinoma cells.

In some instances of the first method, the sorafenib is administered to the cancer cells at a therapeutically effective concentration, the alternating electric field has a field strength of at least 1 V/cm in at least some of the cancer cells, and the applying step has a duration of at least 72 hours.

Another aspect of the invention is directed to a second method of reducing viability of cancer cells disposed in a body of a living subject. The second method comprises administering sorafenib to the subject; and applying an alternating electric field to the cancer cells, the alternating electric field having a frequency between 100 and 400 kHz.

In some instances of the second method, the frequency of the alternating electric field is between 120 and 180 kHz. In some instances of the second method, at least a portion of the applying step is performed simultaneously with at least a portion of the administering step. In some instances of the second method, the cancer cells comprise hepatocellular carcinoma cells. In some instances of the second method, the sorafenib comprises a pharmaceutically acceptable carrier.

In some instances of the second method, the sorafenib is administered to the cancer cells at a therapeutically effective concentration, the alternating electric field has a field strength of at least 1 V/cm in at least some of the cancer cells, and the applying step has a duration of at least 72 hours.

In some instances of the second method, the reduction in viability comprises increasing cytotoxicity in the cancer cells. In some instances of the second method, the reduction in viability comprises decreasing clonogenic survival of the cancer cells. In some instances of the second method, the reduction in viability comprises inducing apoptosis in the cancer cells.

Another aspect of the invention is directed to a third method of reducing the volume of a tumor disposed in a body of a living subject, the tumor including a plurality of cancer cells. The third method comprises administering sorafenib to the subject; and applying an alternating electric field to the cancer cells, the alternating electric field having a frequency between 100 and 400 kHz.

In some instances of the third method, the frequency of the alternating electric field is between 120 and 180 kHz. In some instances of the third method, at least a portion of the applying step is performed simultaneously with at least a portion of the administering step. In some instances of the third method, the cancer cells comprise hepatocellular carcinoma cells.

In some instances of the third method, the sorafenib comprises a pharmaceutically acceptable carrier.

In some instances of the third method, the sorafenib is administered to the cancer cells at a therapeutically effective concentration, the alternating electric field has a field strength of at least 1 V/cm in at least some of the cancer cells, and the applying step has a duration of at least 72 hours.

In some instances of the first, second, and third methods, the sorafenib has the general structure:

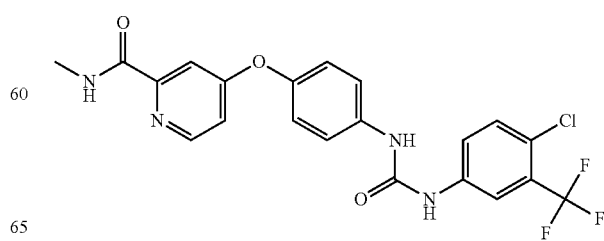

DETAILED DESCRIPTION OF THE PREFERRED EMBODIMENTS

Figure 1:
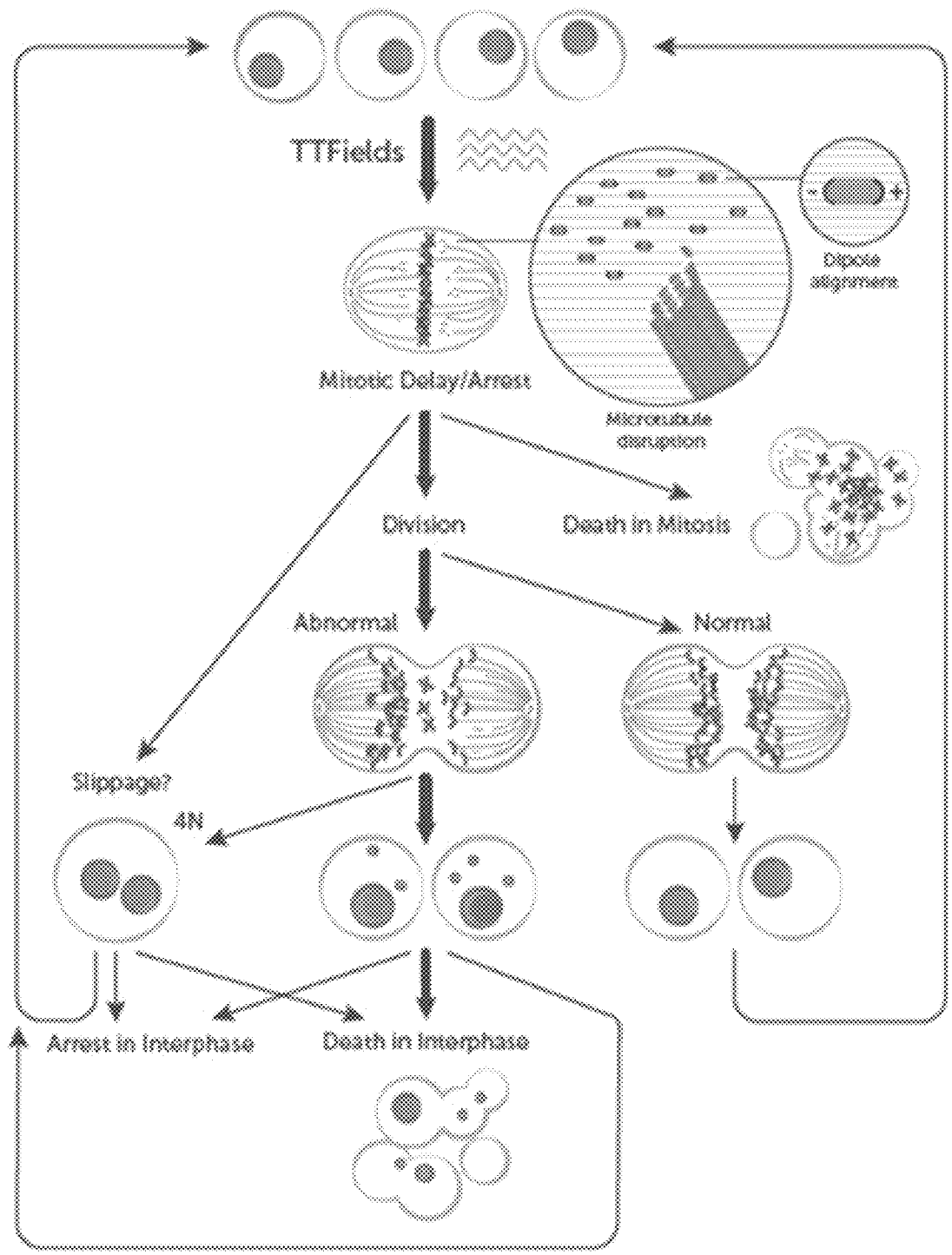
FIG. 1 illustrates the exemplary effects of TTFields on replicating cells.

All references cited herein, including but not limited to patents and patent applications, are incorporated herein by reference in their entirety.

Hepatocellular carcinoma (HCC) is the most common type of primary liver cancer and is a leading cause of cancer-related death worldwide. Sorafenib, an oral multikinase inhibitor that blocks various signalling pathways, is the only first line drug that has been approved for patients with advanced HCC. But the survival benefit of sorafenib is limited.

As described herein, treating HCC with the combination of sorafenib and TTFields provides a synergistic result.

Aspects described herein provide compositions and methods for treating cancer (e.g., HCC) with a combination of TTFields and sorafenib. The term "treating" refers to ameliorating, inhibiting, reducing growth, inhibiting metastases, and prescribing medication to do the same. The term "sorafenib" refers to 4-[4-[[4-chloro-3-(trifluoromethyl)phenyl]carbamoylamino]phenoxy]-N-methylpyridine-2-carboxamide (also known as $C_{21}H_{16}C_{1}F_{3}N_{4}O_{3}$) having the following chemical structure:

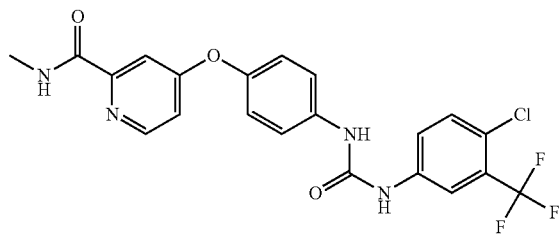 [SMILES: CNC(=O)c1cc(Oc2ccc(NC(=O)Nc3ccc(Cl)c(C(F)(F)F)c3)cc2)ccn1]

and pharmaceutically acceptable salts thereof. Sorafenib can be used in combination with a pharmaceutically acceptable carrier for administration to a patient.

The term "sorafenib" also refers to analogs of sorafenib including small molecules described in U.S. Pat. Nos. 7,235,576; 7,351,834; 7,897,623; 8,124,630; 8,618,141; 8,841,330; 8,877,933; and 9,737,488. The term "analogs" and "variants" of sorafenib refer to molecules that have structural similarity to sorafenib such that the analog or variant retains at least 50% of the activity of sorafenib with respect to cancer cells (e.g., HCC) as described herein.

The term "reducing viability of cancer cells" as used herein, refers to reducing the growth, proliferation, or survival of the cancer cells. In some aspects, the reduction in viability of the cancer cells comprises reducing clonogenic survival of the cancer cells, increasing cytotoxicity of the cancer cells, inducing apoptosis in the cancer cells, and decreasing tumor volume in a tumor formed from at least a portion of the cancer cells.

The term "clonogenic survival" refers to the ability of a single cancer cell to grow into a colony of cancer cells. In one aspect, a "colony" is at least fifty cells.

The term "cytotoxicity" refers to a measure of the ability of drug or treatment to kill a cell.

The term "apoptosis" refers to the phenomena termed "programmed cell death" referring to the death of cell as part of the controlled cell cycle of cell growth and development.

Aspects described herein provide methods of reducing the viability of cancer cells (e.g., hepatocellular carcinoma cells) by administering sorafenib to the cancer cells, and applying an alternating electric field to the cancer cells, the alternating electric field having a frequency between 100 and 400 kHz. In some aspects, at least a portion of the applying step is performed simultaneously with at least a portion of the administering step.

In some aspects, the sorafenib is administered to the cancer cells (e.g., HCC cells) at a therapeutically effective concentration, and the alternating electric field has a field strength of at least 1 V/cm in at least some of the cancer cells.

The term "therapeutically effective concentration," as used herein, refers to the concentration of sorafenib sufficient to achieve its intended purpose (e.g., treatment of cancer, treatment of HCC). In one aspect, a therapeutically effective concentration is at least about 0.5 µM to about 3 µM. In another aspect, a therapeutically effective concentration includes a dosage and dosing regimen as provided on an approved label from a regulatory agency (e.g., US Food and Drug Administration). In a further aspect, the dose of sorafenib provided to a patient in need of treatment is 400 mg in two tablets taken orally twice per day without food.

In another aspect, the step of applying an electrical field has a duration of at least 72 hours. The application of the electrical field for 72 hours may be accomplished in a single 72 hour interval. Alternatively, the application of the electrical field could be interrupted by breaks. For example, 6 sessions with a duration of 12 hours each, with a 2 hour break between sessions.

In yet another aspect, the frequency of the alternating electric field is between 120 and 180 kHz. In another aspect, the sorafenib is administered to the cancer cells at a therapeutically effective concentration, and the alternating electric field has a field strength of at least 1 V/cm in at least some of the cancer cells.

In yet another aspect, the applying step has a duration of at least 72 hours and the frequency of the alternating electric field is between 120 and 180 kHz.

In yet another aspect, at least a portion of the applying step is performed simultaneously with at least a portion of the administering step.

Further aspects provide methods of reducing the viability of cancer cells (e.g., hepatocellular carcinoma cells) disposed in a body of a living subject by administering sorafenib to the subject, and applying an alternating electric field to the cancer cells, the alternating electric field having a frequency between 100 and 400 kHz.

Further aspects provide that at least a portion of the applying step is performed simultaneously with at least a portion of the administering step.

In another aspect, the applying step has a duration of at least 72 hours. The application of the electrical field may be accomplished in a single 72 hour interval or interrupted by breaks, as described above.

In yet another aspect, the frequency of the alternating electric field is between 120 and 180 kHz.

In a further aspect, the sorafenib is administered to the cancer cells at a therapeutically effective concentration, and the alternating electric field has a field strength of at least 1 V/cm in at least some of the cancer cells. Optionally, the applying step has a duration of at least 72 hours and the frequency of the alternating electric field is between 120 and 180 kHz. Optionally, at least a portion of the applying step can be performed simultaneously with at least a portion of the administering step.

In any of the aspects noted above, the reduction in viability may comprise increasing cytotoxicity in the cancer cells (e.g., HCC cells). In any of the aspects noted above, the reduction in viability may comprise decreasing clonogenic survival of the cancer cells (e.g., HCC cells). In any of the aspects noted above, the reduction in viability may comprise inducing apoptosis in the cancer cells (e.g., HCC cells). In any of the aspects noted above, the reduction in viability may comprise decreasing tumor volume in a tumor formed from at least a portion of the cancer cells (e.g., HCC cells).

Results

Frequency Scans in HCC Cell Lines

Figure 2A:
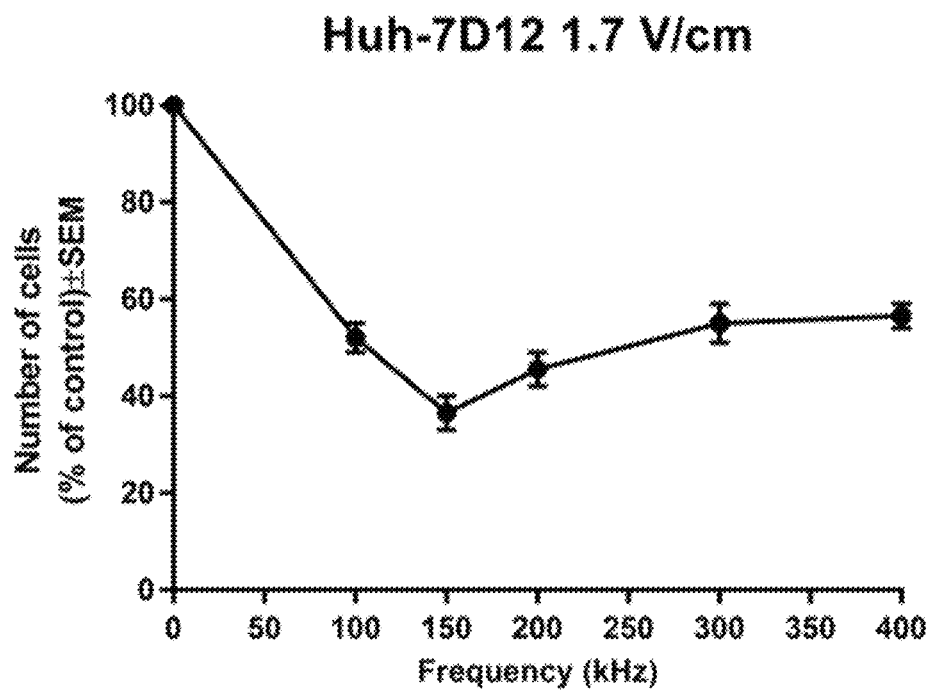
FIGS. 2A-2B show the cytotoxic effect of TTFields frequency scans on HCC cell lines Huh-7D12 and HepG2, respectively.
Figure 2B:
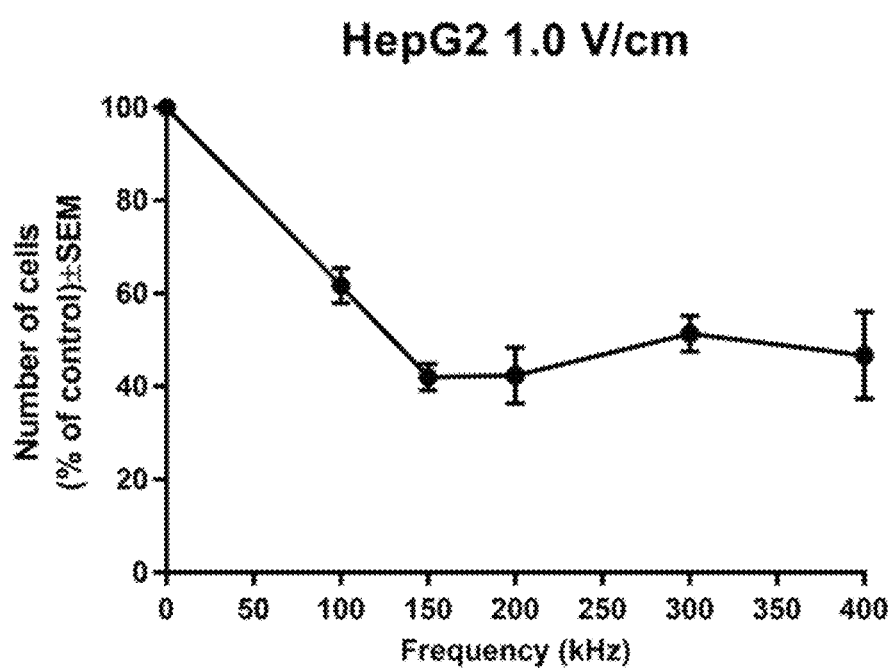

Huh-7D12 cells were found to be less sensitive to TTFields treatment than HepG2 cells. Thus, the TTFields frequency scan experiments with Huh-7D12 cells were performed at 1.7 V/cm RMS instead of 1 V/Cm as shown in FIGS. 2A and 2B. In these experiments, both cell lines were subjected to TTFields at different frequencies to determine which frequency provided the maximum effect. For both cell lines, maximal effect on reducing cell proliferation was obtained at 150 kHz. For the Huh-7D12 cell line, the number of cells at the end of 72 hours of TTFields application (150 kHz, 1.7 V/cm) was 38% of control (FIG. 2A). For the HepG2 cell line, the number of cells at the end of 72 hours of TTFields application (150 kHz, 1 V/cm) was 41% of control (FIG. 2B). Because the maximum sensitivity for both cell lines was found to be 150 kHz, that frequency was used for all subsequent experiments, as described below.

Efficacy of the Combined Treatment of TTFields and Sorafenib

Figure 3A:
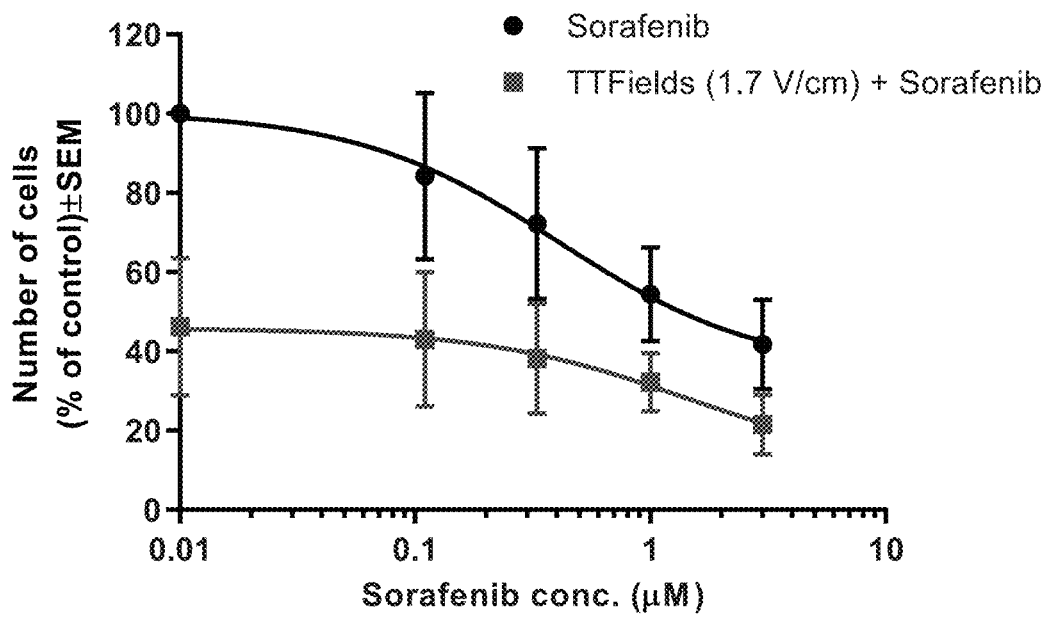
FIGS. 3A-3B illustrate the cytotoxic effect of sorafenib alone and sorafenib combined with TTFields on Huh-7D12 (FIG. 3A) and HepG2 (FIG. 3B) cells.
Figure 3B:
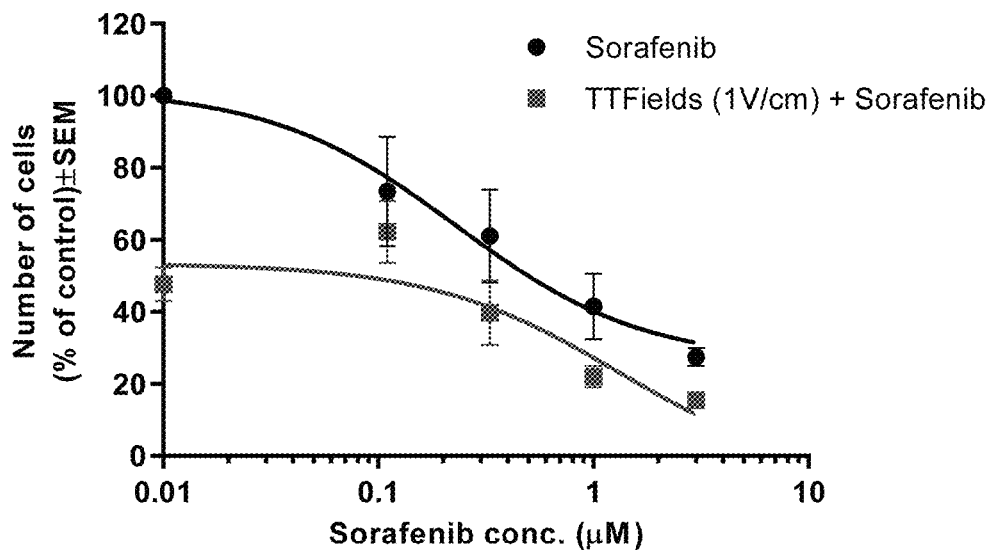

As shown in FIGS. 3A and 3B, both cell lines tested (HepG2, Huh-7D12) were sensitive to treatment with sorafenib with an $IC_{50}$ of around 1.0 µM. All combination experiments were performed at a frequency of 150 kHz. In these examples, the electric field intensity was 1.0 V/cm for HepG2 and 1.7 V/cm for Huh-7D12 cells. Both cell lines were grown at various sorafenib concentrations (0.1-3.0 µM), and were treated with TTFields for 72 hours. The combined treatment of TTFields and sorafenib enhanced cytotoxicity (2-way ANOVA, p<0.001) in both tested cell lines. The number of cells was determined at the end of treatment and is expressed as a percentage of control cells.

Figure 4A:
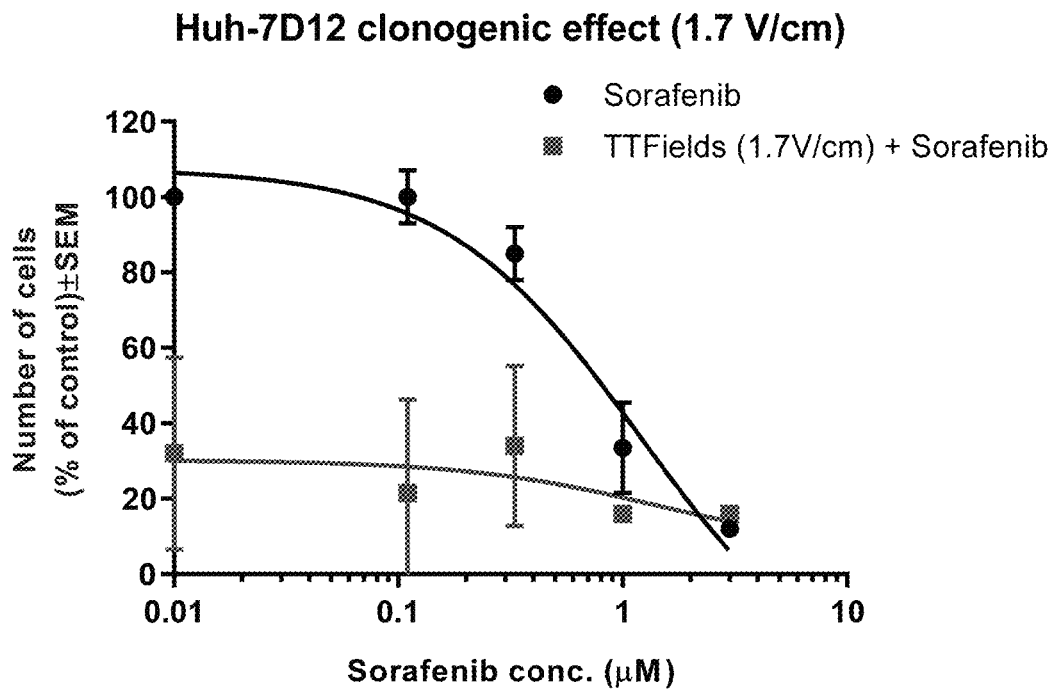
FIGS. 4A-4B illustrate the clonogenic survival of Huh-7D12 (FIG. 4A) and HepG2 (FIG. 4B) cells following treatment of the cells with sorafenib alone and sorafenib combined with TTFields.
Figure 4B:
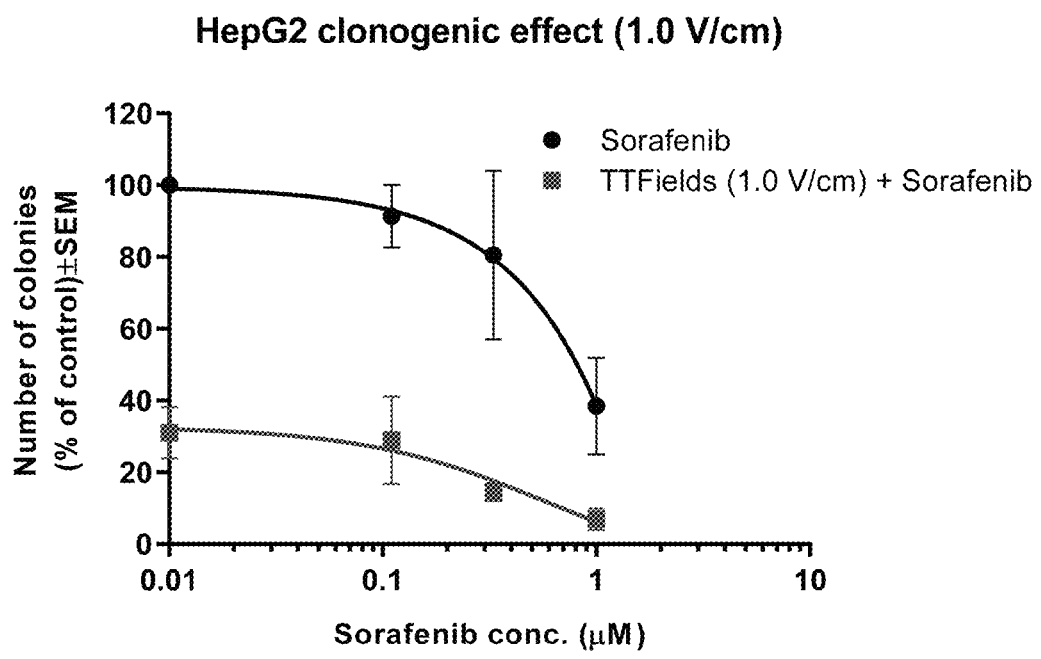

Effect of the Combined Treatment of TTFields and Sorafenib on Cells' Clonogenic Survival As shown in the FIGS. 4A and 4B, response to TTFields application alone led to a 70% reduction in the clonogenic potential for HepG2 cells, and for Huh-7D12 cells (2-way ANOVA, p<0.001). Treatment with sorafenib as a monotherapy, led to a reduction in the clonogenic potential of both cell lines with an escalating dose of the drug. After 72 hours application of the combined treatment of TTFields and sorafenib, additional reduction in the clonogenic survival of HepG2 and Huh-7D12 cells was observed. Notably, there is a synergistic effect between TTFields and sorafenib for reduction of clonogenic potential in an HCC model.

Figure 5A:
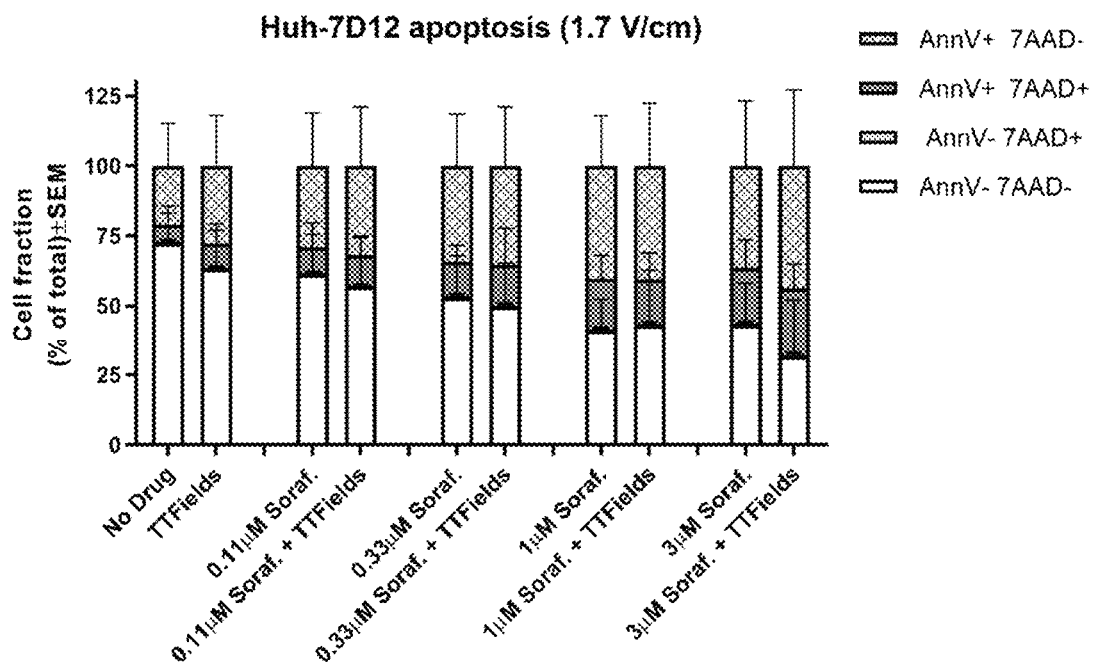
FIGS. 5A-5B illustrate the induction of apoptosis (apoptotic cells as a percentage of total cells) following treatment of Huh-7D12 (FIG. 5A) and HepG2 (FIG. 5B) cells with sorafenib alone and sorafenib combined with TTFields.
Figure 5B:
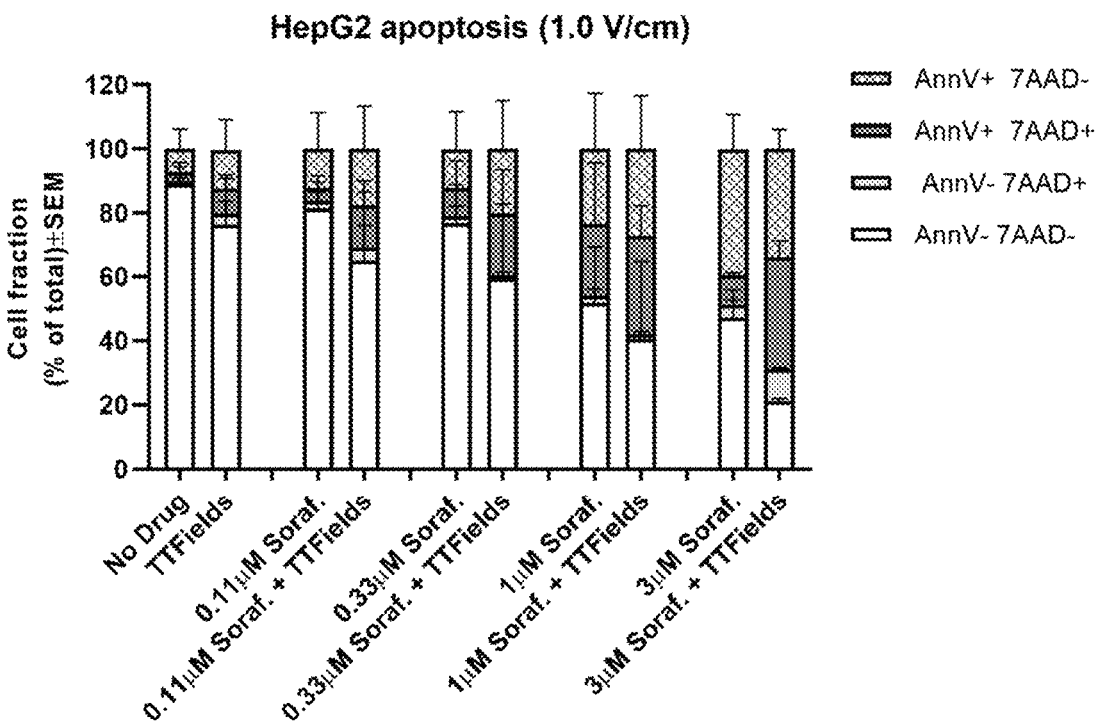

Apoptosis Induction Following the Combined Treatment with TTFields and Sorafenib As shown in FIGS. 5A and 5B, 72 hours sorafenib treatment increased apoptotic events of both HepG2 and Huh-7D12 cells. Apoptosis was measured using FITC Annexin V Apoptosis Detection Kit and 7-AAD (BioLegend, USA). Early, late, and total apoptosis was then quantified using the EC800 flow cytometer (Sony Biotechnology, Japan). As sorafenib concentration increases from no drug to 3 µM, an increasing cell fraction is shown to be positive for apoptosis. The combination of sorafenib with TTFields (1.0 and 1.7 V/cm for HepG2 and Huh-7D12 respectively) led to an additional increase in apoptosis in both cell lines (10-45%). Without being bound by this theory, the latter may explain the observed reduction in the clonogenic potential, demonstrated in the combined treatment.

Figure 6A:
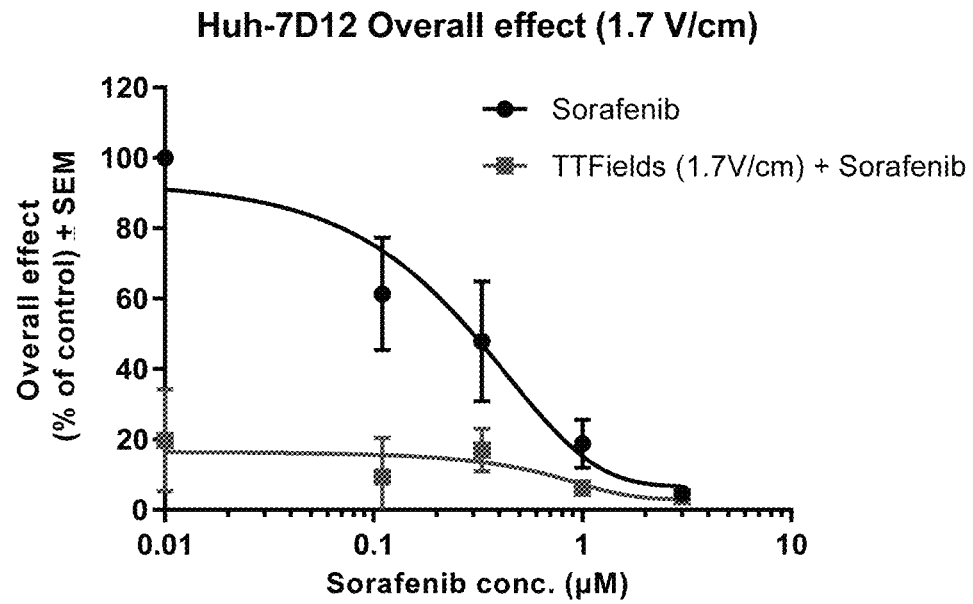
FIG. 6A-6B show the overall effects of sorafenib alone and sorafenib combined with TTFields on Huh-7D12 cells an HepG2 cells, respectively.

FIG. 6A shows the overall effects of sorafenib alone (0.1-3.0 µM) and in combination with TTFields (1.7 V/cm) in Huh-7D12 cells. The improvement provided by TTFields can be seen even at low levels of sorafenib (0.1 µM).

Figure 6B:
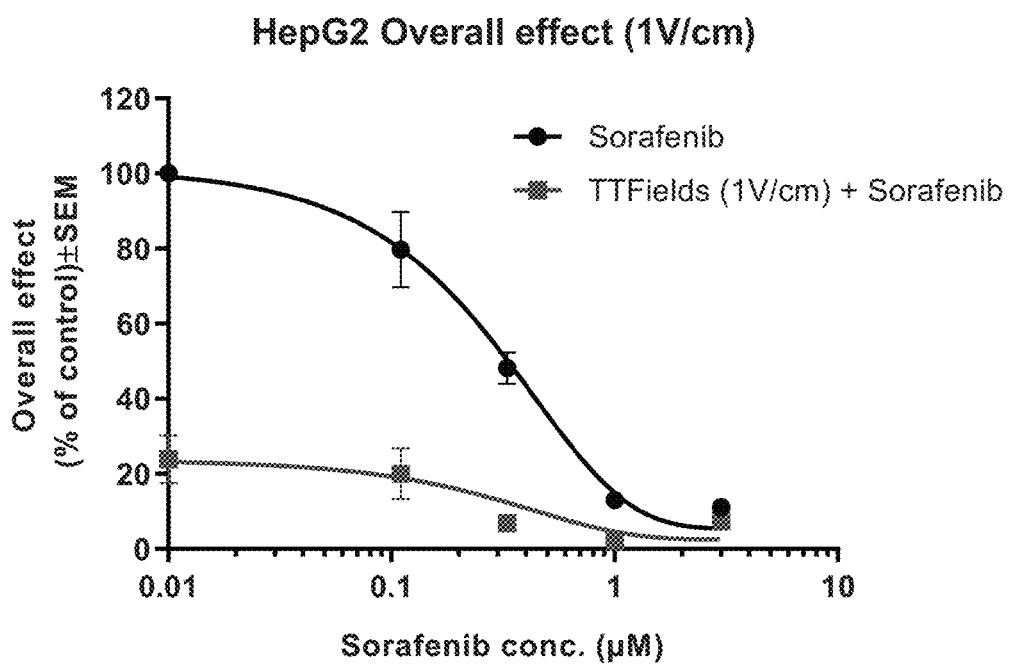

FIG. 6B shows the overall effects of sorafenib alone (0.1-3.0 µM) and in combination with TTFields (1.0 V/cm) in HepG2 cells. The improvement provided by TTFields can be seen even at low levels of sorafenib (0.1 µM).

Figure 7:
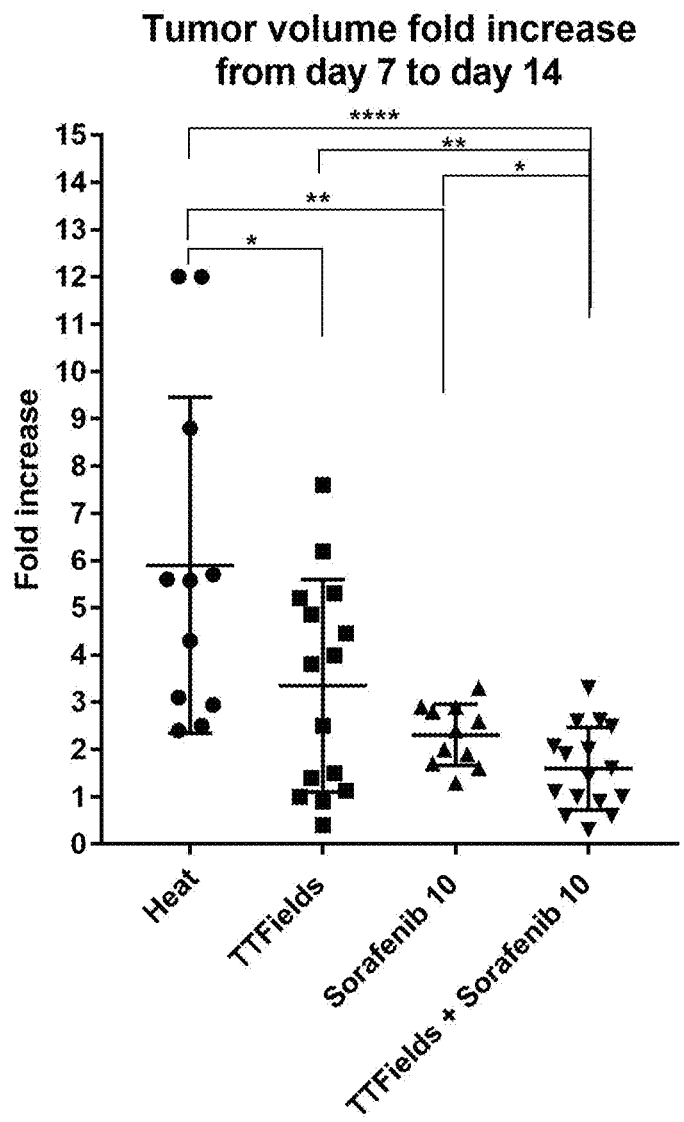
FIG. 7 shows the tumor volume fold increase from day 7 to day 14 in rats following treatment with heat, TTFields alone, sorafenib alone, and TTFields plus sorafenib.
Figure 8:
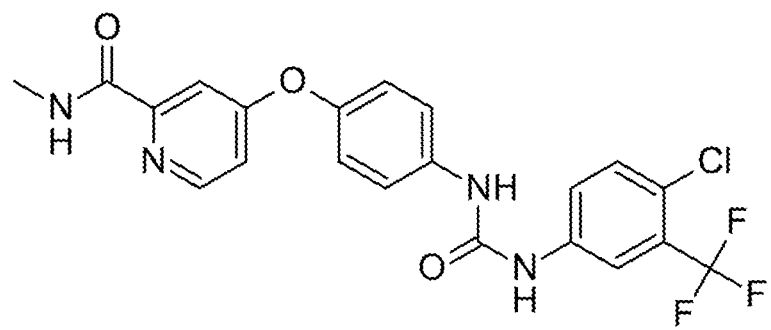
FIG. 8 depicts an example of the chemical structure of sorafenib.

FIG. 7 shows the results of an in vivo study described below with respect to N1S1 tumor volume in Sprague Dawley rats treated with heat, TTFields alone, sorafenib alone, and the combination of TTFields and sorafenib. In this experiment, the volume of the tumor was measured using MRI on day 6 (one day before treatment start) and day 14 (one day after the end of treatment); and each data point in FIG. 7 represents the volume of the tumor on day 14 divided by the volume of the tumor on day 6. Thus, numbers greater than 1 represent growth in the tumor volume, and numbers smaller than 1 represent a tumor that has shrunk between day 6 and day 14. In this figure, "*" represents p<0.1, "" represents p<0.01, and "**" represents p<0.0001. As shown in FIG. 7, there is a synergistic decrease in tumor volume following treatment with a combination of TTFields (2.86 V/cm) and sorafenib (10 mg/kg/day).

These results establish that the viability of cancer cells can be reduced by administering sorafenib to the cancer cells and applying an alternating electric field with a frequency between 100 and 400 kHz to the cancer cells. These results also establish that the viability of cancer cells disposed in a body of a living subject can be reduced by administering sorafenib to the subject and applying an alternating electric field with a frequency between 100 and 400 kHz to the cancer cells. And these results also establish that the volume of a tumor disposed in a body of a living subject can be reduced by administering sorafenib to the subject and applying an alternating electric field with a frequency between 100 and 400 kHz to the cancer cells. In any of these cases, the alternating electric field can be applied before, during, or after the sorafenib treatment. In some aspects, at least a portion of the applying step is performed simultaneously with at least a portion of the administering step.

Note that in the in vitro context, the administering of the sorafenib to the cancer cells (e.g., hepatocellular carcinoma cancer cells) occurs continuously from a first time ($t_1$) when the sorafenib is introduced into the container that is holding the cancer cells until such time ($t_2$) as the sorafenib is removed or exhausted. As a result, if TTFields are applied to the cancer cells between $t_1$ and $t_2$, the applying step will be simultaneous with at least a portion of the administering step.

In the in vivo context, the administering of the sorafenib to the cancer cells can occur continuously from a first time ($t_1$) when the sorafenib is circulating in the patient's body (e.g., after administering it systemically) or introduced into the vicinity of the cancer cells until such time ($t_2$) as the sorafenib is eliminated from the patient's body or exhausted. As a result, if TTFields are applied to the cancer cells between $t_1$ and $t_2$, the applying step will be simultaneous with at least a portion of the administering step. The administration of the sorafenib to the subject may be performed using any of a variety of approaches including but not limited to intravenously, orally, subcutaneously, intrathecal, intraventricularly, and intraperitonealy. And the application of the alternating electric field to the cancer cells may be performed using the Novocure Optune® system or a variant thereof that operates at a different frequency.

For both HCC cell lines tested, HepG2 and Huh-7D12, using TTFields at frequencies between 120 and 180 kHz (e.g., 150 kHz) was effective. The response to TTFields alone (150 kHz, 72 h) led to a significant reduction in the number of cells for both HepG2 and Huh-7D12. In both HepG2 and Huh-7D12 cells, the combination of TTFields and sorafenib led to enhanced efficacy, based on: cytotoxicity (e.g., cell number), clonogenic survival, and the induction of apoptosis.

The in vitro experiments described herein were performed using TTFields combined with sorafenib to reduce the viability of hepatocellular carcinoma cancer cells, and the in vivo experiments described herein were performed using TTFields combined with sorafenib to treat liver cancer (e.g., HCC). But because sorafenib is indicated for certain types of thyroid cancer as well as hepatocellular carcinoma, alternative aspects include using TTFields combined with sorafenib to treat other types of cancers (e.g., thyroid cancer).

Note that while these experiments were performed using the frequencies, field intensities, and durations noted herein, those parameters may be varied. For example, the frequency could be between 100 and 400 kHz or between 120 and 180 kHz; the electric field intensity could be between 0.5 and 5 V/cm; and the duration could be anything longer than 4 hours.

In the in vitro experiments using the Inovitro™ system described herein, the direction of the alternating electric fields was switched at one second intervals between two perpendicular directions. But in alternative embodiments, the direction of the alternating electric fields can be switched at a faster rate (e.g., at intervals between 1 and 1000 ms) or at a slower rate (e.g., at intervals between 1 and 100 seconds).

In the in vitro experiments using the Inovitro™ system described herein, the direction of the alternating electric fields was switched between two perpendicular directions by applying an AC voltage to two pairs of electrodes that are disposed 90° apart from each other in 2D space in an alternating sequence. But in alternative embodiments the direction of the alternating electric fields may be switched between two directions that are not perpendicular by repositioning the pairs of electrodes, or between three or more directions (assuming that additional pairs of electrodes are provided). For example, the direction of the alternating electric fields may be switched between three directions, each of which is determined by the placement of its own pair of electrodes. Optionally, these three pairs of electrodes may be positioned so that the resulting fields are disposed 90° apart from each other in 3D space. In other alternative embodiments, the electrodes need not be arranged in pairs. See, for example, the electrode positioning described in U.S. Pat. No. 7,565,205, which is incorporated herein by reference. In other alternative embodiments, the direction of the field remains constant.

In the in vitro experiments using the Inovitro™ system described herein, the electrical field was capacitively coupled into the culture because the Inovitro™ system uses conductive electrodes disposed on the outer surface of the dish sidewalls, and the ceramic material of the sidewalls acts as a dielectric. But in alternative embodiments, the electric field could be applied directly to the cells without capacitive coupling (e.g., by modifying the Inovitro™ system configuration so that the conductive electrodes are disposed on the sidewall's inner surface instead of on the sidewall's outer surface).

The methods described herein can also be applied in the in vivo context by applying the alternating electric fields to a target region of a live subject's body. This may be accomplished, for example, by positioning electrodes on or below the subject's skin so that application of an AC voltage between selected subsets of those electrodes will impose the alternating electric fields in the target region of the subject's body.

For example, in situations where the relevant cells are located in the subject's liver, one pair of electrodes could be positioned on the front and back of the subject's thorax, and a second pair of electrodes could be positioned on the right and left sides of the subject's thorax. In some embodiments, the electrodes are capacitively coupled to the subject's body (e.g., by using electrodes that include a conductive plate and also have a dielectric layer disposed between the conductive plate and the subject's body). But in alternative embodiments, the dielectric layer may be omitted, in which case the conductive plates would make direct contact with the subject's body. In another embodiment, electrodes could be inserted subcutaneously below a patient's skin. An AC voltage generator applies an AC voltage at a selected frequency (e.g., between 100 and 200 kHz) between the right and left electrodes for a first period of time (e.g. 1 second), which induces alternating electric fields where the most significant components of the field lines are parallel to the transverse axis of the subject's body. Then, the AC voltage generator applies an AC voltage at the same frequency (or a different frequency) between the front and back electrodes for a second period of time (e.g. 1 second), which induces alternating electric fields where the most significant components of the field lines are parallel to the sagittal axis of the subject's body. This two-step sequence is then repeated for the duration of the treatment. Optionally, thermal sensors may be included at the electrodes, and the AC voltage generator can be configured to decrease the amplitude of the AC voltages that are applied to the electrodes if the sensed temperature at the electrodes gets too high. In some embodiments, one or more additional pairs of electrodes may be added and included in the sequence. In alternative embodiments, only a single pair of electrodes is used, in which case the direction of the field lines is not switched. Note that any of the parameters for this in vivo embodiment (e.g., frequency, field strength, duration, direction-switching rate, and the placement of the electrodes) may be varied as described above in connection with the in the vitro embodiments. But care must be taken in the in vivo context to ensure that the electric field remains safe for the subject at all times.

Note that in the experiments described herein, the TTFields were applied for an uninterrupted interval of time (e.g., 72 hours or 14 days). But in alternative embodiments, the application of TTFields may be interrupted by breaks that are preferably short. For example, a 72 hours interval of time could be satisfied by applying the alternating electric fields for six 12 hour blocks, with 2 hour breaks between each of those blocks.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the claims listed below, and equivalents thereof.

Methods

Cell Culture and Drugs

The exemplary effects of the combined treatment of TTFields and sorafenib was tested using the following human HCC cell lines: HepG2 (ATCC) and Huh-7D12 (Sigma). All cells were grown in a humidified incubator supplied with 5% $CO_2$. HepG2 were maintained in EMEM, supplemented with 10% FBS, 2 mmol/L glutamine, Pen-Strep solution (100 units/ml Penicillin and 0.1 mg/ml Streptomycin), 1 mmol/L sodium pyruvate and 1% NEAA. Huh-7D12 cells were maintained in DMEM supplemented with 10% FBS, 2 mmol/L glutamine, Pen-Strep solution (100 units/ml Penicillin and 0.1 mg/ml Streptomycin). Sorafenib was obtained from BioVision, USA.

Cytotoxicity Assay and Overall Effect

TTFields (1.0-1.7 V/cm RMS, 150 kHz) were applied for 72 hours to cell lines using the Inovitro™ system. At the end of treatment, inhibition of tumor cell growth was analysed quantitatively based on cell counts performed on EC800 flow cytometer (Sony Biotechnology, Japan).

Clonogenic Survival

At the end of treatment, cells were removed with trypsin, counted, plated in 6-well plates (300 cells/plate) and incubated for 2-3 weeks in $CO_2$ incubator at 37° C. When colonies reached 40-100 cells/colony, they were fixed with 100% methanol, stained with 0.5% crystal violet (Sigma), photographed, and the number of clones was quantified using ImageJ program.

Apoptosis

For apoptosis analysis, cells were removed with Trypsin immediately after 72 h treatment, washed twice with ice-cold PBS with 1% FBS, and stained using FITC Annexin V Apoptosis Detection Kit and 7-AAD (BioLegend, USA). Early, late, and total apoptosis was then quantified using the EC800 flow cytometer (Sony Biotechnology, Japan).

Statistical Analysis

Data is expressed as mean±standard error (SE), and the statistical significance of differences was assessed using GraphPad Prism 6 software (GraphPad Software, La Jolla, Calif.). Differences between groups were compared using 2-way ANOVA.

EXAMPLES

Example 1

The efficacy of the combined treatment of Sorafenib and TTFields, in the NIS1 orthotopic HCC SD rat model.

TTFields generator, NovoTTF 100A modified for animal experiments, was used to apply the treatment to the animals. Test article is NovoTTF-100A device (HW 4.4x) for which the SW was modified from version 4.24 (released to human use) to SW version 5.5. The SW modification was made in order to allow the device to operate with currents suitable for the treatment of animals (below 600 mAmp).

Specifications and main differences from device used commercially/in clinical trials are summarized in Table 1:

TABLE 1

| Treatment parameters | NovoTTF-100A device release to human use | NovoTTF-100A device used for animal studies |
|---|---|---|
| Frequency | 200 kHz ± 10% | 150 kHz ± 10% |
| Wave form | Sine wave | Sine wave |
| Treatment current | 2000 mAmp ± 20% | 500 mAmp ± 20% |
| Imin | 600 mAmp | 60 mAmp |
| Overheat protection | >41° C. | >41° C. |

The study was be performed in two parts:

In the first part, the efficacy of different Sorafenib concentrations in combination with TTFields was tested, and one concentration was used during future experiments (10 mg/kg/day over 5 days). In the following experiments, the combined treatment of a single Sorafenib concentration and TTFields (150 kHz) was tested.

All animals were injected orthotopically to the left lobe of the liver with N1S1 Hepatocellular Carcinoma model (Garin E. et al., 2005) by day 0 as described in SOP-BI-036. The peritoneum was closed using sutures and the wound was closed using clips. On day 6, all animals underwent first MRI (as described in SOP-BI-029) and were randomly divided into groups.

In the first experiment:
Group I—5 rats were treated with sham heating electrodes and vehicle injection.
Group II—6 rats were treated with 150 kHz TTFields and vehicle injection.
Group III—5 rats were treated with 150 kHz TTFields and 3.3 mg/kg/day Sorafenib.
Group IV—5 rats were treated with 150 kHz TTFields and 10 mg/kg/day Sorafenib.
Group IV—5 rats were treated with 150 kHz TTFields and 30 mg/kg/day Sorafenib.

On day 7, electrodes (TTFields or sham heating) was placed on the animals (as described in SOP-BI-030). Animals were treated for 6 days with TTFields or sham heat. Sorafenib or the control vehicle was administered through IP injection on 5 out of 6 days of treatment. On day 13, all electrodes were removed, and animals underwent a second MRI on day 14. On day 15, all animals started the second duration of treatment. The animals were connected to electrodes for an additional 6 days and underwent daily Sorafenib or vehicle injection (5/6 days).

Throughout treatment, all animals underwent daily clinical examination according to the routine follow-up. Weighing was performed at tumor implantation day (day 0), treatment start day (day 7), electrodes replacement (day 13) and treatment end day (day 21). On day 21, electrodes were removed, and the animals underwent a third MRI. On day 22, the animals were euthanized, the tumors were removed and saved for R&D use.

Example 2

Number, Species, Strain, Sex, Age, Initial Body Weight of Animals

Ninety-eight (98) Sprague Dawley male rats, between 7-8 weeks and between 150-200 grams were provided with an official health certificate from Envigo Ltd. The animals did not exhibit abnormal physiological or behavioral signs before the start of treatment.

Tumor Volume Measurements Using MRI

Tumor volume was determined based on MRI scans on days 7, 14 and day 21 after injection. The MRI system is a Bruker Icon system working at 1 Tesla placed inside the animal facility of the company. Animals were anesthetized with isoflurane and placed prone in a rat body coil. After a localizer image, a T2 weighted coronal anatomical image was scanned with a RARE sequence and the following parameters: TR/TE 1900/51 ms, number of slices 10, slice thickness 1 mm, FOV 55-65 mm, acquisition matrix 140, 8 averages, acquisition time 4 m 18 s. Tumor volume was measured by manual segmentation of the tumor using ITK-SNAP version 3.6.0-rc1 free software.

The experiment was terminated after 22 days. Tumor samples were collected on the following day. The following organs were collected on the following day: Heart, Kidney, Lung, Urinary bladder, Pancreas, Spleen, Liver; Stomach; Duodenum; Jejunum; Ileum; Cecum; Colon, Skin, and bone marrow.

In case a rat weight loss during treatment will be between 15-20%, rat will receive saline infusion and will be disconnected from the electrodes for 24 hours. If rat body weight won't recover to be less than 15% weight loss after 24 hours, the animal will be excluded from the experiment.

Animals were excluded from the study if there was over 20% weight loss.

Sample Preparation and Blood Sampling

Liver tumor samples for R&D use were fixed with 4% Formaldehyde and paraffin embedded. Fixed samples were kept at room temperature in a ventilated clapboard for 3-4 days, then changed for 70% ethanol and transferred to an external expert laboratory for sectioning.

Tissue samples of the following organs were fixed in 4% Formaldehyde: Heart, Kidney, Lung, Urinary bladder, Pancreas, Spleen, Stomach, Duodenum, Jejunum, Ileum, Cecum, Colon, Skin, and bone marrow. Fixed samples were kept at room temperature in a ventilated clapboard for up to one week and then transferred to external expert laboratory for analysis.

Statistical Analysis

Numerical data—Blood exam results, weight and histopathology were averaged for each experimental group. TTFields parameters were averaged for the TTFields treated groups. Student t-test with an alpha level of less than 0.05 was considered a significant difference and calculated between each group.

Example 3—Sorafenib Preparation

Materials:
1. Record all materials details on 'Sorafenib preparation form':
2. Sorafenib Tosylate
3. Ethanol abs
4. Kolliphor EL Cremophore EL
5. PBS-Dulbecco's Phosphate-Buffered Saline Stock Preparation-10 mg/ml:
1. Weigh 80 mg Sorafenib and place it in a 50 ml tube.
2. Mix 1:1-15 ml Ethanol abs and 15 ml Cremophore EL in another 50 ml tube.
3. Add 8 ml mix to the tube with 80 mg Sorafenib.
4. Vortex until Sorafenib dissolves.

Preparation for 8 Rats in Each Group (5+3 Extra):
1 rat=approximately 220 gr→2.2 mg (10 mg/1 kg)
3.3 mg/kg→0.726 mg/rat
10 mg/kg→2.2 mg/rat
30 mg/kg→6.6 mg/rat

TABLE 2

|  | Heat + control | TTFields + control | TTFields 3.3 mg/kg/day | TTFields 10 mg/kg/day | TTFields 30 mg/kg/day |
| --- | --- | --- | --- | --- | --- |
| PBS | 2.7 ml | 2.7 ml | 2.7 ml | 2.7 ml | 2.7 ml |
| Cremophore:ethanol 50:50 | 5.2 ml | 5.2 ml | 4.7 ml | 3.5 ml | — |
| Sorafenib stock 10 mg/ml | — | — | 0.6 ml | 1.8 ml | 5.3 ml |

Vehicle was prepared for Control groups without sorafenib.

REFERENCES

1. Giladi M, et al. Sci Rep 2015; 5:18046.
2. Shteingauz A et al. Cell Death Dis 2018; 9(11):1074. doi: 10.1038/s41419-018-1085-9.
3. Silginer M et al. Cell Death Dis 2017; 8:e2753.
4. Liu L, et al. Can Res 2006; 66:18514858.
5. Liu L, et al. Oncotarget 2017; 8(34):57707-57722.
7. FDA 21 CFR 58 Principles of Good Laboratory Practice, Environmental Health and Safety Publications, Series on Principles of Good Laboratory Practice
8. Franken, N A et. al. Nat Protoc. 2006; 1(5):2315-9
9. Garin E et al., Lab Anim 2005 July; 39(3):314-20.

What is claimed is:

1. A method of reducing viability of cancer cells, the method comprising:
   administering sorafenib to the cancer cells; and
   applying an alternating electric field to the cancer cells, the alternating electric field having a frequency between 100 and 400 kHz,
   wherein the sorafenib is administered to the cancer cells at a therapeutically effective concentration, the alternating electric field has a field strength of at least 1 V/cm in at least some of the cancer cells, and the applying step has a duration of at least 72 hours.

2. The method of claim 1, wherein the frequency of the alternating electric field is between 120 and 180 kHz.

3. The method of claim 1, wherein at least a portion of the applying step is performed simultaneously with at least a portion of the administering step.

4. The method of claim 1, wherein the sorafenib has the general structure:

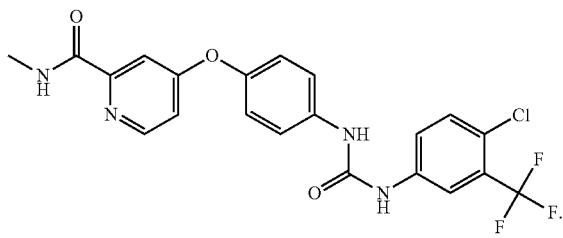 [SMILES: CNC(=O)c1cc(Oc2ccc(NC(=O)Nc3ccc(Cl)c(C(F)(F)F)c3)cc2)ccn1]

5. The method of claim 1, wherein the cancer cells comprise hepatocellular carcinoma cells.

6. The method of claim 1, wherein the applying step is for an uninterrupted interval of time.

7. The method of claim 1, wherein the applying step is interrupted by breaks.

8. A method of reducing viability of cancer cells disposed in a body of a living subject, the method comprising:
administering sorafenib to the subject; and
applying an alternating electric field to the cancer cells, the alternating electric field having a frequency between 100 and 400 kHz,
wherein the sorafenib is administered to the cancer cells at a therapeutically effective concentration, the alternating electric field has a field strength of at least 1 V/cm in at least some of the cancer cells, and the applying step has a duration of at least 72 hours.

9. The method of claim 8, wherein the frequency of the alternating electric field is between 120 and 180 kHz.

10. The method of claim 8, wherein at least a portion of the applying step is performed simultaneously with at least a portion of the administering step.

11. The method of claim 8, wherein the sorafenib has the general structure:

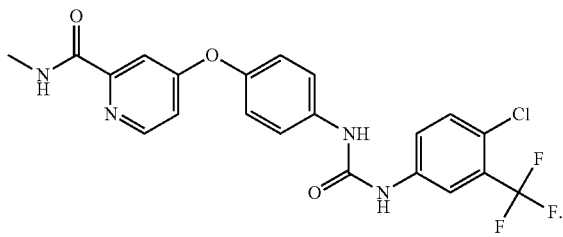 [SMILES: CNC(=O)c1cc(Oc2ccc(NC(=O)Nc3ccc(Cl)c(C(F)(F)F)c3)cc2)ccn1]

12. The method claim 8, wherein the cancer cells comprise hepatocellular carcinoma cells.

13. The method of claim 8, wherein the sorafenib comprises a pharmaceutically acceptable carrier.

14. The method of claim 8, wherein the reduction in viability comprises increasing cytotoxicity in the cancer cells.

15. The method of claim 8, wherein the reduction in viability comprises decreasing clonogenic survival of the cancer cells.

16. The method of claim 8, wherein the reduction in viability comprises inducing apoptosis in the cancer cells.

17. The method of claim 8, wherein the applying step is for an uninterrupted interval of time.

18. The method of claim 8, wherein the applying step is interrupted by breaks.

19. A method of reducing the volume of a tumor disposed in a body of a living subject, the tumor including a plurality of cancer cells, the method comprising:
administering sorafenib to the subject; and
applying an alternating electric field to the cancer cells, the alternating electric field having a frequency between 100 and 400 kHz,
wherein the sorafenib is administered to the cancer cells at a therapeutically effective concentration, the alternating electric field has a field strength of at least 1 V/cm in at least some of the cancer cells, and the applying step has a duration of at least 72 hours.

20. The method of claim 19, wherein the frequency of the alternating electric field is between 120 and 180 kHz.

21. The method of claim 19, wherein at least a portion of the applying step is performed simultaneously with at least a portion of the administering step.

22. The method of claim 19, wherein the sorafenib has the general structure:

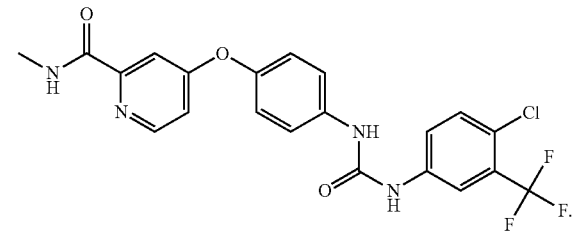 [SMILES: CNC(=O)c1cc(Oc2ccc(NC(=O)Nc3ccc(Cl)c(C(F)(F)F)c3)cc2)ccn1]

23. The method of claim 19, wherein the cancer cells comprise hepatocellular carcinoma cells.

24. The method of claim 19, wherein the sorafenib comprises a pharmaceutically acceptable carrier.

25. The method of claim 19, wherein the applying step is for an uninterrupted interval of time.

26. The method of claim 19, wherein the applying step is interrupted by breaks.

* * * * *